United States Patent [19]

Brunton

[11] Patent Number: 4,879,115

[45] Date of Patent: Nov. 7, 1989

[54] FEED EFFICIENCY IMPROVEMENT COMPOSITION

[75] Inventor: James L. Brunton, Amarillo, Tex.

[73] Assignee: Aerion Industries, Inc., Amarillo, Tex.

[21] Appl. No.: 11,548

[22] Filed: Feb. 6, 1987

[51] Int. Cl.⁴ .................... A61K 33/06; A61K 33/10; A61K 33/08
[52] U.S. Cl. ..................................... 424/694; 424/682
[58] Field of Search ................ 424/154, 156, 157, 159

[56] References Cited

U.S. PATENT DOCUMENTS 3,019,109  1/1962  Klothen ..................................... 92/2
3,022,218  2/1962  Sherman ............................. 424/154
4,610,882  9/1986  Laurent et al. ..................... 424/154

Primary Examiner—Frederick E. Waddell
Attorney, Agent, or Firm—Hubbard, Thurman, Turner & Tucker

[57] ABSTRACT

The feed efficiency of animals is improved by inducing a positive electrical charge in food, including water and other liquids, or in certain components of food.

7 Claims, 1 Drawing Sheet

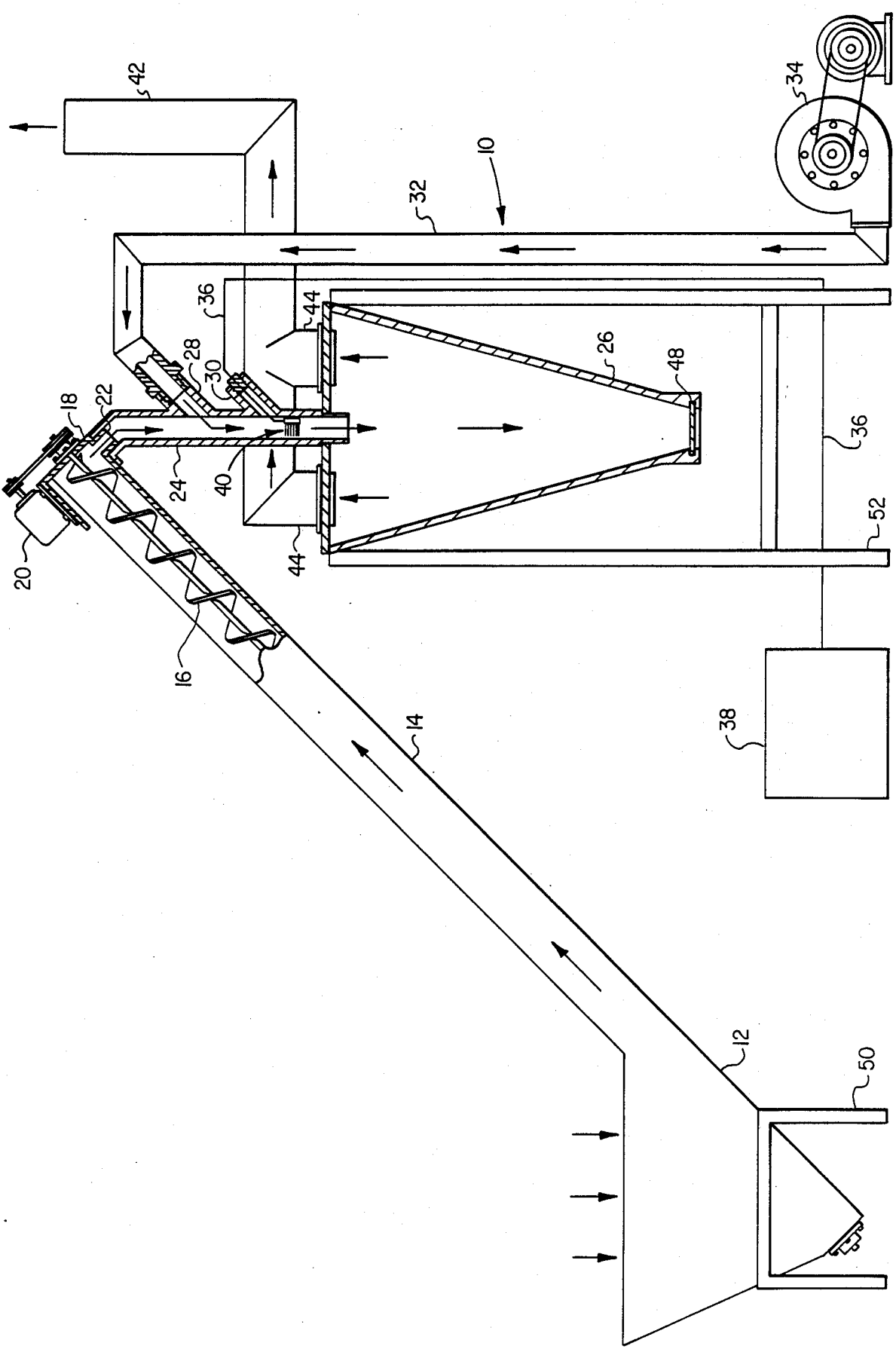

FEED EFFICIENCY IMPROVEMENT COMPOSITION

BACKGROUND OF THE INVENTION

1. Field of the Invention

The present invention relates to a feed composition yielding improved feed efficiency. The composition is produced by inducing a residual electrical charge in livestock feed or in certain components of livestock feed. The composition is especially useful in improving the feed efficiency of cattle.

2. Description of the Prior Art

As long as animals have been raised for the purpose of food production, man has searched for the ideal foods and methods for feeding the animals. Most effort has been directed to identifying foods having a proper nutritional balance which is thought to promote efficient weight gain. Additionally, some attention has been given to the manner of preparing the food, such as cooking, micronizing, flaking, or rolling grain products. Little, if any, attention, however, has been given to the electrical or ionic properties of the food or liquids to be ingested by animals.

The functions of inorganic ions in biological systems have been the subject of many studies. Some of the more important functions of inorganic ions in biological systems include (1) the activation of enzyme systems; (2) the stabilization of proteins in solution; (3) the development of electrical excitability; (4) the regulation of the permeability of membranes and (5) the maintenance of a dynamic state of isotonicity between cells and the extracellular fluid.

The properties of ions depend essentially on their valency and atomic number and hence on their tendency to form complexes with water and organic molecules. Since proteins are large molecules, they have potentially many free positive and negative groups and these may be associated by electrostatic interaction either with water or with ions of opposite charge. The presence of salts in solution modifies these electrostatic associations.

In addition to generalized effects on stereochemistry, certain ions seem to have more specific functions in the activation of enzyme systems. Various types of function are possible. An ion which activates an enzyme may (a) form an integral part of the enzyme molecule; (b) serve to link enzyme and substrate; (c) cause a shift in the equilibrium position of the reaction, or (d) act indirectly by releasing ions which inactivate the enzyme system.

In almost all animals sodium is the main cation of the extracellular fluids. It therefore accounts for the major part of the cation osmotic pressure of the blood and interstitial fluid. Change in the permeability of the cell membranes of excitable cells is responsible for the development of action potentials.

High concentrations of sodium inside cells are deleterious as sodium inhibits some enzyme systems, particularly those associated with glycolysis, and is less active than potassium in activating others. As a monovalent ion sodium tends to offset the action of small amounts of divalent ions in decreasing the permeability of cell membranes.

Potassium is the major cation of cells. In addition to the part it plays in the establishment of the membrane potential of cells it activates certain enzyme systems such as pyruvic phospherase and fructokinase. An adequate concentration of potassium must be present in the extracellular fluid if sodium extrusion from cells is to occur normally. In cells the potassium is not uniformly distributed, its concentration in mitochondria being higher than in the general cell sap.

Perhaps the most important function of calcium is that it decreases the permeability of cell membranes to water and ions. This effect is especially important in the case of excitable tissues. Muscles in calcium free media initially display spontaneous activity, later they lose their excitability. Isolated nerves and muscles swell in salines lacking calcium, probably because the mechanism responsible for the extrusion of sodium can no longer match the faster rate of sodium entry through the more permeable cell membrane. Calcium is also associated with the processes involved in the shortening of the contractile elements of muscles and part at least of this effect is due to the activation of myosin A.T.P.-ase, the enzyme reaction which provides the energy for contraction. Calcium also probably plays some part in the development of action potentials as repetitive stimulation of nerves increases their calcium concentration.

High concentrations of calcium are deleterious to cells as some enzyme systems are inhibited by this ion. Thus it antagonizes the activation of pyrophosphatases by potassium.

As a divalent ion calcium is important in stabilizing colloids particularly the intercellular cement which binds cells together. In this function magnesium behaves similarly though usually less effectively. In the absence of calcium and magnesium cells tend to separate.

Calcium increases the release of the transmitting agent at the neuro-muscular junction of vertebrates and this action is antagonzied by magnesium which inhibits the release of acetyl choline.

When it is present in high concentration, magnesium inhibits the neuro-muscular junction unless sufficient calcium is present to neutralize its effect. Magnesium is present in the cells of terrestrial vertebrates at a concentration of some 50 times that in the blood. It is not uniformly distributed in cells having a higher concentration in the mitochondria and nuclei than in the sap. High concentrations of both magnesium and calcium depress the oxygen consumption of cells, and possibly this effect may be linked to their action in decreasing the permeability of membranes as the effect is offset by increases in the concentration of potassium. Magnesium is an essential activator of many of the enzymes involved in energy transfer, hence its presence in the mitochondria. Among these can be included A.T.P.-ase, pyruvic phosphatase and fructokinase.

With respect to hydrogen ions, the chemical properties of proteins change with pH since they are ampholytes behaving as acids on the alkaline side of their isoelectric point and as acids on the acidic side. The hydration of proteins is governed by the pH, the water absorbed being at a minimum at the isoelectric point. However, as already mentioned, the presence of other ions may modify the degree of hydration. Enzymic activity is usually at its maximum close to but not always at the isoelectric point. Thus pH change may affect a variety of factors such as colloid osmotic pressure, inhibition of water by gels and enzyme activity. An increase in the acidity of the blood is followed by a loss of potassium from cells as a result of an exchange of hydrogen for potassium ions and an inhibition of the sodium pump.

Rather less is known of the functions of inorganic anions apart from the buffering actions of phosphates and bicarbonates in cells and in the blood.

High concentrations of phosphates tend to inhibit calcium actions possibly by lowering the solubility of the calcium. Thus cells are more likely to separate in low calcium media if high concentrations of phosphate are present.

Bicarbonate stimulates the respiration of isolated tissues and the presence of this ion in the bathing medium can increase the extrusion of sodium from cells. Presumably it is for the same reason that the retention of potassium by isolated muscles is improved when bicarbonate is present in the bathing medium.

Although the above-described functions and properties of inorganic ions in biological systems are well known, the ionic valence of components of livestock feed has never been related to the ability of an animal to absorb and utilize the livestock feed.

It is estimated that in the United States alone, 20 million cattle are finished each year for slaughter. The costs of production of beef products continue to increase at an alarming rate. For the production of beef to be competitive with the production of other meat products, the cost of beef production must be held in check. There is, accordingly, a distinct need in the art for methods and products for decreasing the costs of beef production by increasing the growth rate and the feed to gain ratio in cattle.

SUMMARY OF THE INVENTION

The products of the present invention provide an economical manner of promoting efficient and increased rate of gain in animals and especially in cattle.

Accordingly, it is an object of the present invention to provide a feed composition yielding improved feed efficiency.

It is another object of the present invention to provide a feed composition that produces an increased average daily gain in cattle over conventional feed compositions.

It is a further object of the present invention to provide a method and apparatus for producing the feed composition of the present invention.

These and other objects are accomplished by the present invention in which an electrical charge is induced onto livestock feed or components of livestock feed. Positively charged livestock feed or components of livestock feed according to the present invention increased feed efficiency and yields more efficient utilization of the nutrients in the livestock feed or other food products which produces rapid and efficient weight gain.

BRIEF DESCRIPTION OF THE DRAWINGS

In describing the invention, reference will be made to the accompanying drawing which is a perspective view of the apparatus for producing the feed composition of the present invention.

DETAILED DESCRIPTION OF THE PREFERRED EMBODIMENTS

Conventional solid feed and liquids ingested by animals have been found to have a residual negative electrical charge of from about $10^{-7}$ to $10^{-10}$ coulombs. According to the present invention it has been found that by inducing a positive electrical charge on the food or water ingested by livestock the livestock gain weight at a faster and more efficient rate, thereby reducing the cost of weight gain in the livestock. More particularly, it has been found that by rearranging the valence shell and strenghening the positive valency of food or water ingested by livestock, the feed efficiency of such livestock is improved.

It has also been observed that by inducing a positive electrical charge only on certain components of the feed yields better results than attempting to positively charge all of the feed. Limestone containing calcium has been found to be particularly receptive to positive electrical charge and to rearrangement of valence shell electrons. It has been found that when positively charged limestone particles are mixed with conventional feed compositions, a marked increase feeding efficiency is obtained. According to the present invention, those skilled in the art will recognize that any material capable of digestion by animals or humans may be positively charged to affect weight gain efficiency.

Referring now to the drawing, an apparatus for inducing a positive electrical charge onto feed compositions is generally indicated at 10. As shown in the drawing a storage bin 12 for retaining untreated material is in communication with an auger 14. A suitable auger, preferably has a diameter of 4 inches. The auger 14 includes a screw 16 for raising untreated material from storage bin 12 to the elevated end 18 of auger 14. A motor 20 for driving screw 16 is preferably disposed at the elevated end 18 of auger 14. A suitable motor for use in this apparatus is preferably a 1½ horsepower electric motor.

The output port 22 of auger 14 is in fluid communication with a tube 24. Tube 24 includes an upper Y-arm 28 and a lower Y-arm 30. In a preferred embodiment of the present invention upper Y-arm 28, lower Y-arm 30 and the portions of tube 24 below upper Y-arm 28 are constructed from glass. Those of ordinary skill in the art will recognize that other nonconductive materials may suitably be used for these portions. As shown in the drawing, upper Y-arm 28 is in fluid communication with an air duct 32. The air duct 32 is in fluid communication with the air outlet of a blower 34. A suitable blower for use in the apparatus of the present invention is a 5 horsepower electric blower Model 4C131 available from Dayton Manufacturing Co., Chicago, Ill.

The lower Y-arm 30 accomodates a high voltage electrical cable 36. The high voltage electrical cable 36 connects a high voltage power source 38 to a high voltage electrode probe 40. The electrical cable 36 is preferably a high voltage coaxial cable. A suitable power source for use in the apparatus of the present invention is a Spellman regulated high voltage power supply Model RHR100PN100 available from Spellman High-Voltage Electronics Corporation, 7 Fairchild Avenue, Plainview, N.Y. The polarity of this power source is reversible with respect to ground and is adjusted for use according to the invention to be positive with respect to ground. The power source has a maximum 100,000 volt and 2 milliamp output capacity.

The high voltage electrode probe 40 is preferably a stainless steel brush having a plurality of stainless steel bristles. Most preferably, probe 40 is suspended in the center of tube 24 and below lower Y-arm 30 (not shown). The high voltage electrode probe 40 is preferably maintained at a sufficient and effective distance away from collection bin 26 to prevent arcing or bleeding.

As shown in the drawing, an air outlet conduit system 42 communicates with collection bin 26 to provide exhaust means for the air entering collection bin 26 through air duct 32 under the action of blower 34. The air outlet conduit system 42 may include a plurality of inlets 44 to provide for adequate exhaust air flow from collection bin 26. Suitable materials for the air outlet conduit system 42 and inlets 44 are 6 inch diameter PVC conduits.

In a preferred embodiment of the present invention, the collection bin 26 includes an insulator lid 46. The insulator lid 46 is preferably a ¼ inch Micarta sheet. In another preferred embodiment of the present invention, the collection bin 26 includes a sliding gate 48 to allow regulated removal of treated material from collection bin 26. In a further preferred embodiment of the present invention, storage bin 12 is supported by support legs 50 and collection bin 26 is supported by support legs 52. Support legs 50 and support legs 52 are preferably constructed of steel.

The material to be treated and the air are preferably combined at upper Y arm 28 before the combination travels past high voltage electrode probe 40. The material to be treated and air are, preferably, maintained in a substantially anhydrous condition to prevent the electrode probe 40 from arcing to the collection bin 26.

In accordance with the method of the present invention, material to be treated is raised from storage bin 12 to the output port 22 of auger 14 by screw 16. After the material exits output port 22 of auger 14 it enters tube 24 under the influence of gravity. As the material falls through tube 24 it is mixed with air at upper Y-arm 28 and is charged by the high voltage electrode probe 40 thus inducing a residual positive charge in the material. It has been determined that the best results are achieved by increasing the voltage and decreasing the amperage of the power source.

Those skilled in the art will recognize that there are numerous other methods of inducing a positive electric charge on particles and substances, any or all of which may be suitable for the purposes of the present invention.

The amount of charge induced on the treated material can be measured by an electrometer that is capable of measuring infinitesimal amounts of charge down to microamps and nanoamps. A suitable electrometer for use in measuring the amount of charge induced on the treated material is a Keithley Model 600B Electrometer available from Keithley Instruments, Inc., 28775 Aurora Road, Cleveland, Ohio. This device may be used as a coulombmeter and has a range of $10^{-12}$ coulomb at full scale to $10^{-6}$ coulomb.

The feed ingredient samples are placed under and the amount of charge is measured under a Faraday cage. A suitable Faraday cage for use according to the present invention consists of a grounded ¼ inch galvanized wire screen cage of suitable dimensions. The Faraday cage is effective to shield the treated material samples, while measuring the quantity and polarity of the induced charge. This method of measuring the amount of charge of the food product has yielded reproducible readings. The measured amount of charge induced on treated material has ranged from $10^{-7}$ to $10^{-9}$ coulombs.

The present invention may have a significant impact on feeding the human population. By using the present invention, each person could consume less food but obtain the same caloric and/or nutritional content. Using different materials to be charged or changing the polarity of the charge could also cause weight loss in humans.

Various modifications of the disclosed compositions, methods and apparatus of the present invention, as well as alternative modifications, variations and equivalents will become apparent to persons skilled in the art upon reading the above general description. The present invention will now be described in more detail with reference to the following examples. These examples are merely illustrative of the present invention and are not intended to limit the scope of the appended claims, which cover any such modifications, equivalents or variations.

EXAMPLE I

The Effect of the Product of the present invention on Feedlot Performance of Beef Steers Ninety-six beef steers of mixed breeding, weighing an average of 782 lbs., were blocked by weight and assigned to one of 12 pens, with steers in six pens receiving a limestone based premix containing the product of the present invention while the steers in the other six pens received the same premix without the product of the present invention. The treated steers gained weight at a rate 9.6% faster and used 5.7% less feed per lb. of gain than the control steers.

A group of mixed breed beef steers were driven by horseback from a wheat pasture, where they had wintered, to a feedyard in Dumas, Tex., a drive of approximately three miles. At the feedyard, several head were sorted out and 107 head loaded on trucks and hauled to the West Texas State University Experimental Feedlot. Upon arrival they were individually weighed, eartagged, temperatures taken and vaccinated with IBR, PI3, BVD and 7-way Blackleg. Extreme sizes, types and sick appearing cattle were removed so that 96 head remained. These were arrayed by weight with eight of each weight group being assigned to treated and control rations (i.e., blocked by weight). Cattle were not implanted and did not receive an ionophore. The steers were started on a high sorghum silage diet and worked up to a final diet (as fed basis) on June 22, 1984 of 73.75% dry-rolled sorghum, 23.0% sorghum silage, 2% supplement and 1.25% experimental premix.

Since starting weights differed from pen to pen due to the blocking by weight, cattle were weighed off of feed when the average pen weight was thought to be near 1050 lbs., based on previous weights and rates of gain. The average days on feed was 135 days for control steers and 131 days for treated steers. Two consecutive day weights were averaged for the off feed weight. Two treated steers were removed from the experiment, one for water belly and another died, but extensive necropsy ruled out the ration additive.

The results for pens 1 to 12 are shown in Tables 1 to 12, respectively. In Tables 1 to 12, it will be noted that an even distribution of like cattle was achieved based on frame (in hundreds of pounds) and flesh criteria. In Tables 1 to 12, the following abbreviations have the following meanings: DOF means days on feed; HD DAYS means head days; ADG means average daily gain; DMI means dry matter intake; DDMI means daily dry matter intake; and DM/G means dry matter per gain. A statistical analysis of these results are shown in Table 13. Steers receiving the product of the present invention gained weight at a rate 9.6% faster than controls and were 5.7% more efficient in feed conversion.

These differences approached significance (P<0.11) when analyzed on a pen basis. Using each animal as an observation for Average Daily Gain (ADG) reduced the probability of error (P<0.02).

TABLE I

PEN 1 CONTROL (DOF = 113)

| CALF NO. | BREED/ COLOR | FRAME | FLESH | Wt. 6-1 | | Wt. 6/30 | Wt. 7/28 | Wt. 8/25 | Wt. 9/22 | Wt. 9/23 | OFF Wt. |
|---|---|---|---|---|---|---|---|---|---|---|---|
| 3 | A | 5 | 6 | 788 | 794 | 878 | 950 | 968 | 1064 | 1080 | 1072 |
| 30 | RWF | 5 | 5 | 742 | 782 | 852 | 896 | 924 | 1008 | 988 | 998 |
| 48 | B | 5 | 5 | 750 | 756 | 180 | 926 | 972 | 1052 | 1052 | 1052 |
| 50 | BRAN | 6 | 5 | 728 | 742 | 846 | 932 | 1000 | 1100 | 1112 | 1106 |
| 55 | JH | 6 | 5 | 742 | 760 | 872 | 918 | 1000 | 1038 | 1074 | 1056 |
| 60 | EX X | 6.5 | 5 | 758 | 770 | 880 | 954 | 962 | 1040 | 1052 | 1046 |
| 89 | BWF | 6 | 4.5 | 760 | 790 | 902 | 966 | 1052 | 1144 | 1150 | 1147 |
| 98 | BX | 7 | 4 | 770 | 778 | 894 | 952 | 1004 | 1078 | 1056 | 1067 |
| TOTAL WT. | | | | 6038 | | 7004 | 7494 | 7882 | 8524 | 8564 | 8544 |
| AVE WT. | | | | 754.75 | | 875.5 | 936.8 | 985.3 | 1065.5 | 1070.5 | 1068 |
| GAIN PERIOD | | | | | | 966 | 490 | 388 | 642 | | 662 |
| HD DAYS | | | | | | 224 | 224 | 224 | 224 | | 232 |
| ADG | | | | | | 4.313 | 2.19 | 1.73 | 2.87 | | 2.85 |
| TOTAL HD DAYS | | | | | | | 448 | 672 | 896 | | 904 |
| TOTAL GAIN | | | | | | | 1456 | 1844 | 2486 | | 2506 |
| TO DATE ADG | | | | | | | 3.25 | 2.74 | 2.77 | | 2.77 |
| PERIOD DMI | | | | | | 5314 | 5527 | 5372 | 5143 | | |
| PERIOD DDMI | | | | | | 23.72 | 24.67 | 23.98 | 22.96 | | |
| PERIOD DM/G | | | | | | 5.50 | 11.28 | 13.85 | 8.01 | | |
| TOTAL DMI | | | | | | 5314 | 10841 | 16213 | 21356 | | 21782 |
| TOTAL DDMI | | | | | | 23.72 | 24.20 | 24.13 | 23.83 | | 24.3 |
| TOTAL DM/G | | | | | | 5.5 | 7.45 | 8.79 | 8.59 | | 8.69 |

TABLE 2

PEN 2 CONTROL (DOF = 132)

| CALF NO. | BREED/ COLOR | FRAME | FLESH | Wt. 6-1 | | Wt. 6/30 | Wt. 7/28 | Wt. 8/25 | Wt. 9/22 | Wt. 10/11 | Wt. 10/12 | Off Wt. |
|---|---|---|---|---|---|---|---|---|---|---|---|---|
| 9 | BWF | 5.5 | 5 | 710 | 698 | 824 | 914 | 962 | 986 | 1070 | 1074 | 1072 |
| 16 | B | 5 | 5 | 718 | 728 | 818 | 832 | 874 | 924 | 982 | 972 | 977 |
| 17 | A | 5.5 | 5 | 706 | 724 | 798 | 884 | 942 | 1008 | 1080 | 1084 | 1082 |
| 31 | BMF | 5 | 4.5 | 720 | 738 | 826 | 936 | 986 | 1072 | 1136 | 1140 | 1138 |
| 32 | A | 5 | 5.5 | 702 | 700 | 806 | 888 | 936 | 986 | 1046 | 1032 | 1039 |
| 40 | A | 5 | 5 | 706 | 712 | 768 | 832 | 902 | 946 | 1020 | 1022 | 1021 |
| 52 | B | 5 | 5 | 716 | 734 | 810 | 864 | 932 | 942 | 992 | 1026 | 1009 |
| 82 | BRAN | 5 | 5 | 700 | 708 | 852 | 962 | 1036 | 1114 | 1162 | 1166 | 1164 |
| TOTAL WT. | | | | 5678 | | 6502 | 7112 | 7570 | 7978 | 8488 | 8516 | 8502 |
| AVE WT. | | | | 709.75 | | 812.75 | 889 | 846.3 | 997.2 | 1061 | 1064.5 | 1062.8 |
| GAIN PERIOD | | | | | | 824 | 610 | 458 | 408 | | | 524 |
| HD DAYS | | | | | | 224 | 224 | 224 | 224 | | | 160 |
| ADG PERIOD | | | | | | 3.679 | 2.72 | 2.045 | 1.82 | | | 3.28 |
| TOTAL HD DAYS | | | | | | | 448 | 672 | 896 | | | 1056 |
| TOTAL GAIN | | | | | | | 1434 | 1892 | 2300 | | | 2824 |
| TO DATE ADG | | | | | | | 3.20 | 2.82 | 2.57 | | | 2.67 |
| PERIOD DMI | | | | | | 5241 | 4601 | 4705 | 4589 | | | |
| PERIOD DDMI | | | | | | 23.40 | 20.54 | 21.00 | 20.49 | | | |
| PERIOD DM/G | | | | | | 6.36 | 7.54 | 10.27 | 11.25 | | | |
| TOTAL DMI | | | | | | 5241 | 9842 | 14547 | 19136 | | | 22387 |
| TOTAL DDMI | | | | | | 23.4 | 21.97 | 21.65 | 21.36 | | | 21.2 |
| TOTAL DM/G | | | | | | 6.36 | 6.86 | 7.69 | 8.32 | | | 7.93 |

TABLE 3

PEN 3 CONTROL (DOF = 141)

| CALF No. | BREED/ COLOR | FRAME | FLESH | Wt. 6-1 | | Wt. 6/30 | Wt. 7/28 | Wt. 8/25 | Wt. 9/22 | Wt. 10/20 | Wt. 10/21 | Off Wt. |
|---|---|---|---|---|---|---|---|---|---|---|---|---|
| 24 | H | 5 | 4 | 690 | 678 | 796 | 804 | 870 | 894 | 948 | 928 | 938 |
| 27 | RWF | 5 | 5 | 698 | 702 | 766 | 868 | 854 | 912 | 918 | 918 | 918 |
| 34 | H | 6.5 | 3.5 | 694 | 678 | 764 | 812 | 834 | 932 | 932 | 928 | 930 |
| 41 | SH X | 6 | 4 | 678 | 688 | 790 | 856 | 878 | 990 | 1022 | 984 | 1003 |
| 58 | A | 5 | 5 | 694 | 688 | 836 | 856 | 850 | 936 | 996 | 980 | 988 |
| 62 | H | 6 | 4 | 682 | 690 | 706 | 810 | 856 | 966 | 1022 | 1020 | 1021 |
| 81 | A | 5 | 5 | 682 | 690 | 816 | 912 | 934 | 1046 | 1086 | 1086 | 1086 |
| 104 | Chi X | 7 | 3 | 690 | 674 | 828 | 892 | 938 | 1076 | 1076 | 1076 | 1076 |
| TOTAL WT. | | | | 5508 | | 6302 | 6810 | 7014 | 7692 | 8000 | 7920 | 7960 |
| AVE WT. | | | | 688.5 | | 787.75 | 851.3 | 876.8 | 961.5 | 1000 | 990 | 995 |
| GAIN PERIOD | | | | | | 794 | 508 | 204 | 678 | | | 268 |
| HD DAYS | | | | | | 224 | 224 | 224 | 224 | | | 232 |

TABLE 3-continued

PEN 3 CONTROL (DOF = 141)

| CALF No. | BREED/ COLOR | FRAME | FLESH | Wt. 6-1 | Wt. 6/30 | Wt. 7/28 | Wt. 8/25 | Wt. 9/22 | Wt. 10/20 | Wt. 10/21 | Off Wt. |
|---|---|---|---|---|---|---|---|---|---|---|---|
| ADG PERIOD | | | | | 3.545 | 2.27 | .91 | 3.03 | | | 1.15 |
| TOTAL HD DAYS | | | | | | 448 | 672 | 896 | | | 1128 |
| TOTAL GAIN | | | | | | 1302 | 1506 | 2184 | | | 2452 |
| TO DATE ADG | | | | | | 2.91 | 2.24 | 2.44 | | | 2.17 |
| PERIOD DMI | | | | | 4598 | 4177 | 4394 | 4183 | | | |
| PERIOD DDMI | | | | | 20.53 | 18.65 | 19.62 | 18.67 | | | |
| PERIOD DM/G | | | | | 5.79 | 8.22 | 21.54 | 6.17 | | | |
| TOTAL DMI | | | | | 4598 | 8775 | 13169 | 17352 | | | 21815 |
| TOTAL DDMI | | | | | 20.53 | 19.59 | 19.60 | 19.37 | | | 19.3 |
| TOTAL DM/G | | | | | 5.79 | 6.74 | 8.74 | 7.95 | | | 8.90 |

TABLE 4

PEN 4 CONTROL (DOF = 141)

| CALF NO. | BREED/ COLOR | FRAME | FLESH | Wt. 6-1 | Wt. 6/30 | Wt. 7/28 | Wt. 8/25 | Wt. 9/22 | Wt. 10/20 | Wt. 10/21 | Off Wt. |
|---|---|---|---|---|---|---|---|---|---|---|---|
| 2 | BWF | 5 | 5 | 654 | 660 | 738 | 842 | 872 | 956 | 1038 | 1036 | 1037 |
| 22 | H | 5 | 5 | 668 | 668 | 774 | 852 | 924 | 998 | 1078 | 1074 | 1076 |
| 26 | H | 5 | 5 | 672 | 676 | 780 | 892 | 914 | 1014 | 1076 | 1070 | 1073 |
| 37 | H | 5 | 4 | 668 | 676 | 806 | 892 | 952 | 1028 | 1070 | 1070 | 1070 |
| 56 | H | 5 | 5 | 674 | 684 | 776 | 858 | 928 | 978 | 1056 | 1046 | 1051 |
| 65 | B | 5 | 4 | 656 | 668 | 756 | 858 | 880 | 920 | 1016 | 1006 | 1011 |
| 66 | JH | 4.5 | 5 | 658 | 680 | 776 | 862 | 934 | 964 | 1070 | 1034 | 1052 |
| 84 | B | 5 | 4 | 660 | 676 | 772 | 830 | 894 | 970 | 1038 | 1028 | 1033 |
| TOTAL WT. | | | | 5310 | | 6178 | 6886 | 7298 | 7828 | 8442 | 8364 | 8403 |
| AVE WT. | | | | 663.75 | | 772.25 | 860.8 | 912.3 | 978.5 | 1055.3 | 1045.5 | 1050.4 |
| GAIN PERIOD | | | | | | 868 | 708 | 412 | 530 | | | 575 |
| HD DAYS | | | | | | 224 | 224 | 224 | 224 | | | 232 |
| ADG PERIOD | | | | | | 3.875 | 3.16 | 1.84 | 2.37 | | | 2.48 |
| TOTAL HD DAYS | | | | | | | 448 | 672 | 896 | | | 1128 |
| TOTAL GAIN | | | | | | | 1576 | 1988 | 2518 | | | 3093 |
| TO DATE ADG | | | | | | | 3.52 | 2.96 | 2.81 | | | 2.74 |
| PERIOD DMI | | | | | | 4666 | 4717 | 5001 | 4504 | | | |
| PERIOD DDMI | | | | | | 20.83 | 21.05 | 22.33 | 20.11 | | | |
| PERIOD DM/G | | | | | | 5.38 | 6.66 | 12.14 | 8.50 | | | |
| TOTAL DMI | | | | | | 4666 | 9383 | 14384 18888 | | | 23857 | |
| TOTAL DDMI | | | | | | 20.83 | 20.94 | 21.40 | 21.08 | | | 21.1 |
| TOTAL DM/G | | | | | | 5.38 | 5.95 | 7.24 | 7.50 | | | 7.71 |

TABLE 5

PEN 5 CONTROL (DOF = 141)

| CALF NO. | BREED/ COLOR | FRAME | FLESH | Wt. 6-1 | Wt. 6/30 | Wt. 7/28 | Wt. 8/25 | Wt. 9/22 | Wt. 10/20 | Wt. 10/21 | Off Wt. |
|---|---|---|---|---|---|---|---|---|---|---|---|
| 10 | HoCX | 5 | 5 | 646 | 654 | 784 | 814 | 904 | 946 | 982 | 996 | 989 |
| 23 | A | 4 | 5.5 | 636 | 652 | 732 | 808 | 848 | 890 | 952 | 952 | 952 |
| 25 | BRAN | 6.5 | 3.5 | 640 | 646 | 732 | 792 | 812 | 866 | 902 | 904 | 903 |
| 49 | B | 4.5 | 5 | 646 | 666 | 764 | 808 | 866 | 950 | 994 | 990 | 992 |
| 53 | LH | 4.5 | 5 | 632 | 646 | 738 | 834 | 868 | 910 | 950 | 950 | 950 |
| 73 | B | 5.5 | 4 | 622 | 614 | 724 | 792 | 892 | 956 | 1010 | 1026 | 1018 |
| 74 | H | 5.5 | 5 | 638 | 650 | 740 | 816 | 840 | 874 | 928 | 902 | 915 |
| 90 | A | 4.5 | 5 | 632 | 632 | 746 | 788 | 874 | 890 | 950 | 950 | 950 |
| TOTAL WT. | | | | 5092 | | 5960 | 6452 | 6904 | 7282 | 7668 | 7670 | 7669 |
| AVE WT. | | | | 636.5 | | 745.0 | 806.5 | 863.0 | 910.2 | 958.5 | 958.75 | 958.6 |
| GAIN PERIOD | | | | | | 868 | 492 | 452 | 378 | | | 387 |
| HD DAYS | | | | | | 224 | 224 | 224 | 224 | | | 232 |
| ADG PERIOD | | | | | | 3.875 | 2.20 | 2.02 | 1.69 | | | 1.67 |
| TOTAL HD DAYS | | | | | | | 448 | 672 | 896 | | | 1128 |
| TOTAL GAIN | | | | | | | 1360 | 1812 | 2190 | | | 2577 |
| TO DATE ADG | | | | | | | 3.04 | 2.70 | 2.44 | | | 2.28 |
| PERIOD DMI | | | | | | 4727 | 4387 | 4475 | 3896 | | | |
| PERIOD DDMI | | | | | | 21.10 | 19.58 | 19.98 | 17.39 | | | |
| PERIOD DM/G | | | | | | 5.45 | 8.92 | 9.90 | 10.31 | | | |
| TOTAL DMI | | | | | | 4727 | 9114 | 13589 | 17485 | | | 22124 |
| TOTAL DDMI | | | | | | 21.10 | 20.34 | 20.22 | 19.51 | | | 19.6 |
| TOTAL DM/G | | | | | | 5.45 | 6.70 | 7.50 | 7.98 | | | 8.58 |

TABLE 6

PEN 6 CONTROL (DOF = 141)

| CALF NO. | BREED/ COLOR | FRAME | FLESH | Wt. 6-1 | | Wt. 6/30 | Wt. 7/28 | Wt. 8/25 | Wt. 9/22 | Wt. 10/20 | Wt. 10/21 | Off Wt. |
|---|---|---|---|---|---|---|---|---|---|---|---|---|
| 11 | SH X | 5 | 5 | 618 | 616 | 676 | 672 | 708 | 784 | 786 | 790 | 788 |
| 59 | H | 4.5 | 4 | 594 | 596 | 692 | 778 | 842 | 878 | 864 | 866 | 865 |
| 61 | H | 4.5 | 5 | 584 | 590 | 662 | 768 | 840 | 932 | 1008 | 998 | 1003 |
| 83 | BX | 6.5 | 2.5 | 614 | 644 | 768 | 892 | 974 | 1000 | 1012 | 996 | 1004 |
| 86 | BX | 5 | 5 | 606 | 600 | 684 | 732 | 772 | 806 | 858 | 856 | 857 |
| 91 | BWF | 4 | 4 | 558 | 588 | 652 | 748 | 802 | 860 | 908 | 908 | 908 |
| 92 | H | 5 | 4 | 568 | 576 | 684 | 746 | 846 | 924 | 978 | 966 | 972 |
| 106 | LH X | 6.5 | 2.5 | 600 | 636 | 700 | 802 | 864 | 938 | 984 | 988 | 986 |
| TOTAL WT. | | | | 4742 | | 5518 | 6138 | 6648 | 7122 | 7398 | 7368 | 7383 |
| AVE WT. | | | | 592.75 | | 689.75 | 767.3 | 831.0 | 890.2 | 924.8 | 921 | 922.9 |
| GAIN PERIOD | | | | | | 776 | 620 | 510 | 474 | | | 261 |
| HD DAYS | | | | | | 224 | 224 | 224 | 224 | | | 232 |
| ADG PERIOD | | | | | | 3.464 | 2.77 | 2.28 | 2.12 | | | 1.125 |
| TOTAL HD DAYS | | | | | | | 448 | 672 | 896 | | | 1128 |
| TOTAL GAIN | | | | | | | 1396 | 1906 | 2380 | | | 2641 |
| TO DATE ADG | | | | | | | 3.12 | 2.84 | 2.66 | | | 2.34 |
| PERIOD DMI | | | | | | 4226 | 4086 | 3931 | 3603 | | | |
| PERIOD DDMI | | | | | | 18.87 | 18.24 | 17.55 | 16.08 | | | |
| PERIOD DM/G | | | | | | 5.45 | 6.59 | 7.71 | 7.60 | | | |
| TOTAL DMI | | | | | | 4226 | 8312 | 12243 | 15846 | | | 19683 |
| TOTAL DDMI | | | | | | 18.87 | 18.55 | 18.22 | 17.69 | | | 17.4 |
| TOTAL DM/G | | | | | | 5.45 | 5.95 | 6.42 | 6.66 | | | 7.45 |

TABLE 7

PEN 7 TREATED (DOF = 98)

| CALF NO. | BREED/ COLOR | FRAME | FLESH | Wt. 6-1 | | Wt. 6/30 | Wt. 7/28 | Wt. 8/25 | Wt. 9/7 | Wt. 9/8 | Off Wt. |
|---|---|---|---|---|---|---|---|---|---|---|---|
| 5 | BWF | 6 | 5 | 740 | 748 | 854 | 908 | 1006 | 1020 | 1010 | 1015 |
| 28 | EX | 7.5 | 3.5 | 782 | 792 | 966 | 1056 | 1142 | 1180 | 1176 | 1178 |
| 36 | CX | 7 | 4 | 738 | 764 | 854 | 954 | 982 | 992 | 970 | 981 |
| 43 | H | 5.5 | 5 | 750 | 742 | 814 | 924 | 986 | 1002 | 1010 | 1006 |
| 45 | BMF | 5.5 | 5.5 | 746 | 770 | 886 | 974 | 1022 | 1066 | 1056 | 1061 |
| 57 | H | 6 | 4 | 746 | 760 | 862 | 946 | 998 | 1036 | 1018 | 1027 |
| 64 | H | 5 | 4.5 | 776 | 790 | 912 | 1006 | 1068 | 1070 | 1070 | 1070 |
| 67 | A | 4.5 | 6.5 | 756 | 770 | 888 | 944 | 996 | 1008 | 990 | 999 |
| TOTAL WT. | | | | 6034 | | 7016 | 7712 | 8200 | 8374 | 8300 | 8337 |
| AVE WT. | | | | 754.25 | | 877.0 | 964 | 1025 | 1046.8 | 1037.5 | 1042.1 |
| GAIN PERIOD | | | | | | 982 | 696 | 488 | | | 137 |
| HD DAYS | | | | | | 224 | 224 | 224 | | | 112 |
| ADG PERIOD | | | | | | 4.384 | 3.11 | 2.18 | | | 1.22 |
| TOTAL HD DAYS | | | | | | | 448 | 672 | | | 784 |
| TOTAL GAIN | | | | | | | 1678 | 2166 | | | 2303 |
| TO DATE ADG | | | | | | | 3.75 | 3.22 | | | 2.94 |
| PERIOD DMI | | | | | | 5039 | 4874 | 5322 | | | |
| PERIOD DDMI | | | | | | 22.50 | 21.76 | 23.76 | | | |
| PERIOD DM/G | | | | | | 5.13 | 7.00 | 10.91 | | | |
| TOTAL DMI | | | | | | 5039 | 9913 | 15235 | | | 17851 |
| TOTAL DDMI | | | | | | 22.50 | 22.13 | 22.67 | | | 22.8 |
| TOTAL DM/G | | | | | | 5.13 | 5.91 | 7.03 | | | 7.75 |

TABLE 8

PEN 8 TREATED (DOF = 132)

| CALF NO. | BREED/ COLOR | FRAME | FLESH | Wt. 6-1 | | Wt. 6/30 | Wt. 7/28 | Wt. 8/25 | Wt. 9/22 | Wt. 10/11 | Wt. 10/12 | Off Wt. |
|---|---|---|---|---|---|---|---|---|---|---|---|---|
| 19 | A | 5 | 5 | 706 | 716 | 784 | 874 | 940 | 990 | 1108 | 1088 | 1098 |
| 35 | H | 5 | 5 | 698 | 706 | 802 | 864 | 908 | 962 | 1040 | 1020 | 1030 |
| 68 | JH | 4.5 | 5 | 716 | 742 | 824 | 918 | 982 | 1040 | 1130 | 1114 | 1122 |
| 71 | H | 6 | 4 | 716 | 726 | 838 | 936 | 1016 | 1060 | 1144 | 1120 | 1132 |
| 72 | BWF | 6 | 4.5 | 724 | 714 | 874 | 822 | 908 | 970 | 1082 | 1060 | 1071 |
| 85 | A | 5 | 4.5 | 706 | 712 | 820 | 932 | 1004 | 1052 | 1170 | 1160 | 1165 |
| 94 | BWF | 6.5 | 4 | 710 | 716 | 828 | 966 | 1030 | 1064 | 1194 | 1188 | 1191 |
| 96 | BRAN | | | 704 | 710 | 798 | 770 | 826 | 884 | 966 | 960 | 963 |
| TOTAL WT. | | | | 5680 | | 6568 | 7082 | 7614 | 8022 | 8834 | 8710 | 8772 |
| AVE WT. | | | | 710.0 | | 821.0 | 885.3 | 951.8 | 1003 | 1104 | 1088.8 | 1096.5 |
| GAIN PERIOD | | | | | | 888 | 514 | 532 | 408 | | | 750 |
| HD DAYS | | | | | | 224 | 224 | 224 | 224 | | | 160 |
| ADG PERIOD | | | | | | 3.964 | 2.29 | 2.375 | 1.82 | | | 4.69 |
| TOTAL HD DAYS | | | | | | | 448 | 672 | 896 | | | 1056 |
| TOTAL GAIN | | | | | | | 1402 | 1934 | 2342 | | | 3092 |
| TO DATE ADG | | | | | | | 3.13 | 2.88 | 2.61 | | | 2.93 |

TABLE 8-continued

| | | | | PEN 8 TREATED (DOF = 132) | | | | | | | |
|---|---|---|---|---|---|---|---|---|---|---|---|
| CALF NO. | BREED/ COLOR | FRAME | FLESH | Wt. 6-1 | Wt. 6/30 | Wt. 7/28 | Wt. 8/25 | Wt. 9/22 | Wt. 10/11 | Wt. 10/12 | Off Wt. |
| PERIOD DMI | | | | | 4875 | 4432 | 4887 | 4468 | | | |
| PERIOD DDMI | | | | | 21.76 | 19.79 | 21.82 | 19.95 | | | |
| PERIOD DM/G | | | | | 5.49 | 8.62 | 9.19 | 10.95 | | | |
| TOTAL DMI | | | | | 4875 | 9307 | 14194 | 18662 | | | 22409 |
| TOTAL DDMI | | | | | 21.76 | 20.77 | 21.12 | 20.83 | | | 21.2 |
| TOTAL DM/G | | | | | 5.49 | 6.64 | 7.34 | 7.97 | | | 7.25 |

TABLE 9

| | | | | PEN 9 TREATED (DOF = 132) | | | | | | | |
|---|---|---|---|---|---|---|---|---|---|---|---|
| CALF NO. | BREED/ COLOR | FRAME | FLESH | Wt. 6-1 | Wt. 6/30 | Wt. 7/28 | Wt. 8/25 | Wt. 9/22 | Wt. 10/11 | Wt. 10/12 | Off Wt. |
| 12 | H | 5.5 | 5 | * | 714 | * | — | — | — | — | — |
| 14 | RMF | 5 | 5 | 694 | 680 | 808 | 876 | 950 | 1028 | 1086 | 1086 |
| 21 | BMF | 6 | 4 | 686 | 666 | 830 | 892 | 958 | 1022 | 1110 | 1102 | 1106 |
| 46 | H | 6.5 | 4 | 690 | 720 | 794 | 884 | 944 | 1022 | 1116 | 1116 | 1116 |
| 69 | H | 5 | 5 | 690 | 710 | 796 | 880 | 920 | 982 | 1048 | 1030 | 1039 |
| 78 | A | 4.5 | 6.5 | 678 | 684 | 786 | 834 | 904 | 964 | 10022 | 1000 | 1001 |
| 80 | BX | 6 | 4 | 694 | 696 | 790 | 840 | 956 | 1024 | 1098 | 1090 | 1094 |
| 87 | A | 5 | 5 | 682 | 710 | 830 | 900 | 964 | 1050 | 1086 | 1070 | 1078 |
| TOTAL WT. | | | | 4814* | | 5634* | 6106 | 6596 | 7092 | | | 7520 |
| AVE WT. | | | | | | 804.86* | 872.3 | 942.3 | 1013.1 | | | 1074.3 |
| GAIN PERIOD | | | | 687.71* | | 820 | 472 | 490 | 496 | | | 428 |
| HD DAYS | | | | | | 196* | 196 | 196 | 196 | | | 140 |
| ADG PERIOD | | | | | | 4.18* | 2.41 | 2.50 | 2.53 | | | 3.06 |
| TOTAL HD DAYS | | | | | | | 392 | 588 | 784 | | | 924 |
| TOTAL GAIN | | | | | | | 1292 | 1782 | 2278 | | | 2706 |
| TO DATE ADG | | | | | | | 3.30 | 3.03 | 2.91 | | | 2.93 |
| PERIOD DMI | | | | | | 4227* | 4505 | 4469 | 4054 | | | |
| PERIOD DOMI | | | | | | 21.57 | 22.98 | 22.80 | 2068 | | | |
| PERIOD DM/G | | | | | | 5.15* | 9.54 | 9.12 | 8.17 | | | |
| TOTAL DMI | | | | | | 4227 | 8732 | 13201 | 17255 | | | 21053 |
| TOTAL DDMI | | | | | | 21.57 | 22.28 | 22.45 | 22.01 | | | 22.8 |
| TOTAL DM/G | | | | | | 5.15 | 6.76 | 7.41 | 7.57 | | | 7.78 |

Calf no. 12 was removed on July 19, 1986 due to water belly. Removed feed.

TABLE 10

| | | | | PEN 10 TREATED (DOF = 141) | | | | | | | |
|---|---|---|---|---|---|---|---|---|---|---|---|
| CALF NO. | BREED/ COLOR | FRAME | FLESH | Wt. 6-1 | Wt. 6/30 | Wt. 7/28 | Wt. 8/25 | Wt. 9/22 | Wt. 10/20 | Wt. 10/21 | Off Wt. |
| 29 | H | 6 | 4.5 | 656 | 654 | 832 | 832 | 884 | 954 | 992 | 976 | 984 |
| 39 | B | 7 | 3 | 676 | 694 | 782 | 840 | 884 | 932 | 982 | 986 | 984 |
| 44 | A | 4.5 | 5 | 670 | 676 | 780 | 848 | 902 | 972 | 1008 | 1018 | 1013 |
| 47 | B | 6.5 | 3 | 672 | 698 | 780 | 878 | 926 | 956 | 998 | 986 | 992 |
| 51 | H | 4.5 | 4.5 | 654 | 654 | 730 | 836 | 990 | 1036 | 1022 | 1029 | |
| 70 | CX | 6 | 4.5 | 666 | 660 | 756 | 854 | 898 | 982 | 1048 | 1048 | 1048 |
| 103 | BX | 7 | 4 | 656 | 634 | 790 | 870 | 970 | 1072 | 1114 | 1122 | 1118 |
| 105 | BX | 6.5 | 3 | 664 | 658 | 760 | 860 | 924 | 984 | 994 | 998 | 996 |
| TOTAL WT. | | | | 5314 | | 6142 | 6818 | 7284 | 7832 | 8172 | 8156 | 8164 |
| AVE WT. | | | | 664.25 | | 767.75 | 852.3 | 910.5 | 979 | 1021.5 | 1019.5 | 1020.5 |
| GAIN PERIOD | | | | | | 828 | 676 | 466 | 548 | | | 332 |
| HD DAYS | | | | | | 224 | 224 | 224 | 224 | | | 232 |
| ADG PERIOD | | | | | | 3.696 | 3.02 | 2.08 | 2.45 | | | 1.43 |
| TOTAL HD DAYS | | | | | | | 448 | 672 | 896 | | | 1128 |
| TOTAL GAIN | | | | | | | 1504 | 1970 | 2518 | | | 2850 |
| TO DATE ADG | | | | | | | 3.36 | 2.93 | 2.81 | | | 2.53 |
| PERIOD DMI | | | | | | 4873 | 4749 | 5056 | 4409 | | | |
| PERIOD DDMI | | | | | | 21.75 | 21.20 | 22.57 | 19.68 | | | |
| PERIOD DM/G | | | | | | 5.89 | 7.03 | 10.85 | 8.04 | | | |
| TOTAL DMI | | | | | | 4873 | 9622 | 14678 | 19087 | | | 23392 |
| TOTAL DDMI | | | | | | 21.75 | 21.48 | 21.84 | 21.30 | | | 20.7 |
| TOTAL DM/G | | | | | | 5.89 | 6.40 | 7.45 | 7.58 | | | 8.21 |

TABLE 11

| | | | | PEN 11 TREATED (DOF = 141) | | | | | | | |
|---|---|---|---|---|---|---|---|---|---|---|---|
| CALF NO. | BREED/ COLOR | FRAME | FLESH | Wt. 6-1 | Wt. 6/30 | Wt. 7/28 | Wt. 8/25 | Wt. 9/22 | Wt. 10/20 | Wt. 10/21 | Off Wt. |
| 7 | A | 5 | 5 | 638 | 652 | 730 | 778 | 806 | 870 | 932 | 934 | 933 |
| 8 | H | 5 | 4 | 622 | 650 | 724 | 804 | 856 | 940 | 1022 | 1014 | 1018 |

TABLE 11-continued

PEN 11 TREATED (DOF = 141)

| CALF NO. | BREED/ COLOR | FRAME | FLESH | Wt. 6-1 | | Wt. 6/30 | Wt. 7/28 | Wt. 8/25 | Wt. 9/22 | Wt. 10/20 | Wt. 10/21 | Off Wt. |
|---|---|---|---|---|---|---|---|---|---|---|---|---|
| 18 | A | 4 | 5 | 632 | 632 | 758 | 818 | 878 | 960 | 1026 | 1016 | 1021 |
| 54 | H | 5 | 5 | 652 | 640 | 766 | 850 | 898 | 946 | 1032 | 1016 | 1024 |
| 63 | H | 5 | 5 | 642 | 648 | 756 | 858 | 874 | 980 | 1052 | 1052 | 1052 |
| 76 | BX | 7 | 2.5 | — | 652 | died | — | — | — | — | — | — |
| 88 | H | 6 | 4 | 648 | 682 | 764 | 804 | 872 | 952 | 1064 | 1038 | 1051 |
| 100 | BX | 6 | 3 | 638 | 630 | 746 | 840 | 934 | 1036 | 1100 | 1084 | 1092 |
| TOTAL WT. | | | | 4472 | | 5244 | 5752 | 6118 | 6684 | 7228 | 7154 | 7191 |
| AVE WT. | | | | 639.25 | | 749.14 | 821.7 | 874 | 954.9 | 1032.6 | 1022 | 1027.3 |
| GAIN PERIOD | | | | | | 772 | 508 | 366 | 566 | | | 507 |
| HD DAYS | | | | | | 196 | 196 | 196 | 196 | | | 203 |
| ADG PERIOD | | | | | | 3.939 | 2.59 | 1.87 | 2.89 | | | 2.5 |
| TOTAL HD DAYS | | | | | | | 392 | 588 | 784 | | | 987 |
| TOTAL GAIN | | | | | | | 1280 | 1646 | 2212 | | | 2719 |
| TO DATE ADG | | | | | | | 3.27 | 2.80 | 2.82 | | | 2.75 |
| PERIOD DMI | | | | | | 3979* | 4340 | 4004 | 4122 | | | |
| PERIOD DDMI | | | | | | 23.24 | 22.14 | 20.43 | 21.03 | | | |
| PERIOD DM/G | | | | | | 5.90 | 8.54 | 10.94 | 7.28 | | | |
| TOTAL DMI | | | | | | 3979 | 8319 | 12323 | 16445 | | | 21605 |
| TOTAL DDMI | | | | | | 23.24 | 21.22 | 20.96 | 20.98 | | | 21.9 |
| TOTAL DM/G | | | | | | 5.90 | 6.50 | 7.49 | 7.43 | | | 7.95 |

Calf no. 76 died on June 30, 1986 and was removed-Assumed did not eat last 3 days.

TABLE 12

PEN 12 TREATED (DOF = 141)

| CALF NO. | BREED COLOR | FRAME | FLESH | Wt. 6-1 | | Wt. 6/30 | Wt. 7/28 | Wt. 8/25 | Wt. 9/22 | Wt. 10/20 | Wt. 10/21 | Off Test |
|---|---|---|---|---|---|---|---|---|---|---|---|---|
| 1 | JH | 4 | 5 | 620 | 602 | 726 | 766 | 828 | 902 | 930 | 912 | 921 |
| 4 | RMF | 5 | 5 | 606 | 610 | 686 | 776 | 842 | 916 | 996 | 984 | 990 |
| 13 | BWF | 4 | 5 | 550 | 570 | 650 | 768 | 798 | 894 | 982 | 974 | 978 |
| 33 | RWF | 5.5 | 4 | 596 | 610 | 726 | 796 | 874 | 944 | 968 | 960 | 964 |
| 38 | B | 4 | 3 | 572 | 582 | 638 | 684 | 694 | 734 | 772 | 764 | 768 |
| 75 | H | 5 | 5 | 602 | 614 | 712 | 770 | 808 | 870 | 934 | 926 | 930 |
| 79 | A | 5 | 5 | 598 | 592 | 654 | 718 | 818 | 880 | 930 | 928 | 929 |
| 95 | C | 7 | 3 | 582 | 600 | 706 | 792 | 856 | 922 | 998 | 972 | 985 |
| TOTAL WT. | | | | 4726 | | 5498 | 6070 | 6518 | 7062 | 7510 | 7420 | 7465 |
| AVE WT. | | | | 590.75 | | 687.25 | 758.8 | 815 | 883 | 938.8 | 927.5 | 933.1 |
| GAIN PERIOD | | | | | | 772 | 572 | 448 | 544 | | | 403 |
| HD DAYS | | | | | | 224 | 224 | 224 | 224 | | | 232 |
| ADG PERIOD | | | | | | 3.446 | 2.55 | 2.00 | 2.43 | | | 1.74 |
| TOTAL AD DAYS | | | | | | | 448 | 672 | 896 | | | 1128 |
| TOTAL GAIN | | | | | | | 1344 | 1792 | 2336 | | | 2739 |
| TO DATE ADG | | | | | | | 3.00 | 2.67 | 2.61 | | | 2.43 |
| PERIOD DMI | | | | | | 4785 | 4071 | 3866 | 3819 | | | |
| PERIOD DDMI | | | | | | 21.36 | 18.17 | 17.26 | 17.05 | | | |
| PERIOD DM/G | | | | | | 6.20 | 7.12 | 8.63 | 7.02 | | | |
| TOTAL DMI | | | | | | 4785 | 8856 | 12722 | 16541 | | | 20157 |
| TOTAL DDMI | | | | | | 21.36 | 19.77 | 18.93 | 18.46 | | | 17.9 |
| TOTAL DM/G | | | | | | 6.20 | 6.59 | 7.10 | 7.08 | | | 7.36 |

TABLE 13

The Effect of the Product of the Present Invention on Feedlot Performance of Beef Steers

| Item | Control | Treated | Prob. |
|---|---|---|---|
| No. of steers | 48 | 46 | |
| Initial Wt. (lb) | 780 | 784 | |
| Ending Wt. (lb) | 1010 | 1032 | |
| A.D.G. | 2.49 | 2.73 = 9.6% | .11[1] |
| D.M. intake (lb) | 20.3 | 21.1 = 103.9% | .54 |
| D.M./gain | 8.18 | 7.71 = 5.7% | .11 |

[1] (P < .02) when each animal used as an observation

EXAMPLE 2

Growth Promotion Screening Trial

The objective of this example was to explore the benefits of feeding a premix containing the product of the present invention on growth rate and feed conversion of finishing steers.

Sixty-four head of mixed breed steers from wheat pasture were used in this trial. The cattle arrived and were processed the next day. Processing involved the following procedures:

(1) Clostridium chauvoei-septicum novyi-sordellii bacterin-toxoid from Affiliated Laboratories, Bristol, Tenn. 37620, serial number 6313, and expiration date 10 Apr., 1986 (5 ml/head).

(2) A-D injection, Durvet, Blue Springs, Mo. 46015 (2 ml/head), 500,000 IU vitamin A, and 75,000 IU D3 per ml.

(3) Bovine rhinotracheitis-virus diarrhea-parainfluenza 3 vaccine haemophilus somnus-pasteurella haemolytica-multocida bacterin. (IBR-BVD-P13/Bar Somnus-2P) Anchor Laboratories Incorporated, St. Joseph, Mo. 64502, serial number 102-127-156-017B, expiration date Mar. 18, 1985.

(4) Ivomec 1% injection for cattle, MSD AgVet, Merck and Company, Incorporated, Rahway, N.J.

07065, dose was 6 ml/head, lot number KBC 009, expiration date June, 1985.

The cattle were pre-shrunk two days in a row and the average of this weight is the beginning weight. The arrival, processing, shrunk, and first day filled weights are presented in Table 14.

TABLE 14

Arrival, Processing, and Shrunk Weights for Trial

| Pen | Arrival Weight | Processing Weight | First Shrunk Weight | Second Shrunk Weight | Average Shrunk Weight | Filled Weight Day Study Beginning |
|---|---|---|---|---|---|---|
| 1 | 643.8 | 638.0 | 608.5 | 620.8 | 614.6 | 638.2 |
|   | 52.3$^a$ | 58.8 | 56.2 | 53.2 | 54.4 | 58.5 |
| 2 | 640.0 | 629.2 | 609.4 | 598.6 | 604.0 | 629.0 |
|   | 52.6 | 44.9 | 45.6 | 41.8 | 43.4 | 41.5 |
| 7 | 644.6 | 637.2 | 612.2 | 599.5 | 605.9 | 634.5 |
|   | 44.0 | 46.0 | 43.8 | 48.3 | 45.9 | 61.7 |
| 8 | 645.9 | 642.6 | 616.6 | 618.5 | 617.6 | 640.8 |
|   | 50.3 | 55.7 | 52.4 | 52.5 | 52.3 | 70.3 |
| Total | 643.6 | 636.8 | 611.7 | 609.5 | 610.5 | 635.6 |
|   | 48.8 | 50.7 | 48.7 | 49.2 | 48.4 | 57.7 |

$^a$standard deviation

The cattle were housed in pens with individual feed monitoring devices. (Pin Pointer AIS Cookeville, Tenn.) The cattle were individually ear tagged with a unique number and a special tag as part of the monitoring system.

The treatments were on a limestone carrier and fed at the rate of 25 lbs. per ton of feed. The control was from the same supply of limestone. The ration fed is illustrated in Table 15.

TABLE 15

Diet Fed During Study

| Ingredients | % as is |
|---|---|
| Rolled Corn | 77.93 |
| Cottonseed Hulls | 10.00 |
| Cottonseed Meal | 6.00 |
| Cone Molasses | 5.00 |
| Potassium Chloride | .50 |
| Ammonium Sulfate | .30 |
| Salt | .25 |
| Vitamin A 20 mil/lb | .01 |
| Trace Minerals | .01 |

The feed was sampled each week and assayed for moisture, protein, fat, fiber, ash, phosphorus, and calcium. The feed was analyzed 3 times during the study and the other feed samples stored. The analyses were completed by A-L Laboratories in Lubbock, Tex. Table 16 illustrates the average analysis for the samples. The feed did not contain an ionophore nor were the cattle implanted.

TABLE 16

Average analysis for feed samples on dry basis

| | Control | Treated |
|---|---|---|
| Moisture | 13.80 | 13.72 |
| Protein | 11.07 | 11.37 |
| Fat | 3.03 | 3.13 |
| Fiber | 6.51 | 7.17 |
| Ash | 11.16 | 11.10 |
| Phosphorus | .23 | .19 |
| Calcium | 1.20 | 1.00 |

One calf died during the study.

Table 17 illustrates the average daily gain for calves through slaughter. Twelve of the treated steers were killed before 154 days.

TABLE 17

Average Daily Gains pounds during trial

| Days | Control | Treated |
|---|---|---|
| 1–28 | 4.96 | 5.02 |
| 1–56 | 3.54 | 3.88 |
| 1–84 | 3.34 | 3.45 |
| 1–112 | 2.86 | 3.01 |
| 1–kill | 2.47$^a$ | 2.90$^b$ |

$^{a,b}$Different superscripts indicate significant differences (P < .05)

The feed intakes are presented in Table 18. No significant difference in feed intake occurred.

TABLE 18

The feed Intakes for Trial, as is

| Days | Control | Treated |
|---|---|---|
| 1–28 | 19.1 (2.79) | 19.5 (2.79) |
| 1–56 | 19.6 (2.73) | 19.6 (2.71) |
| 1–84 | 20.6 (2.72) | 20.3 (2.68) |
| 1–112 | 20.7 (2.66) | 20.3 (2.60) |
| 1–kill | 20.8 (2.49) | 20.5 (2.54) |

The feed to gain ratios are illustrated in Table 19.

TABLE 19

The Feed to Gain Ratios for Trial

| Days | Control | Treated |
|---|---|---|
| 1–28 | 3.85 | 3.97 |
| 1–56 | 5.74 | 5.17 |
| 1–84 | 6.21 | 5.95 |
| 1–112 | 7.29 | 6.82 |
| 1–kill | 8.50$^a$ | 7.19$^b$ |

$^{a,b}$Different superscripts indicate significant differences (P < .05).

The feed conversion was significantly better when the product was added to the feed.

It is of interest to determine how different starting weights respond to the product (Table 20).

TABLE 20

Performance by beginning weight

| Begining Weight | N | Treatment | Feed to Gain | Average Daily Gain |
|---|---|---|---|---|
| 500 | 6 | Control | 9.18$^a$ | 2.57$^a$ |
|  | 3 | Treated | 7.26$^b$ | 3.35$^b$ |
| 600 |  | Control | 8.64$^a$ | 2.74$^a$ |
|  |  | Treated | 7.15$^b$ | 2.27$^b$ |
| 700 | 7 | Control | 7.55 | 2.40 |
|  | 5 | Treated | 7.36 | 2.55 |

$^{a,b}$Different superscripts indicate significant differences (P < .05).

When the product of the present invention was incorporated into the ration as prescribed, the cattle responded with increased average daily gain and a decrease in feed to gain conversion. It is noted that the heavy animals did not respond as well as the 600 or 500 pound steers. This would indicate that the lighter cattle benefitted more from longer periods of time on processed feed.

EXAMPLE 3

Sixty-four head of beef steers, weighing an average of 700 lbs. were assigned to one of four pens with pin pointer feeders. A treatment group of 32 head received feed containing the product of the present invention while a control group of 32 head received feed not containing the product of the present invention. All sixty-four head of steers were monitored for 154 days while on this feed. The results at the end of 154 days were as follows:

|  | ADG | Feed/Gain |
|---|---|---|
| Treatment | 2.90 lbs. | 7.9 |
| Control | 2.47 lbs. | 8.5 |
| % Response | +17.4% | −15.4% |

While the present invention has been described in detail and with reference to specific examples thereof, it will be apparent to one skilled in the art that various changes and modifications can be made therein without departing from the spirit and scope thereof.

What is claimed is:

1. A composition for increasing growth rate and decreasing feed to gain ratio in animals comprising: feeds having a proper nutritional balance and a strengthened positive valency of the feeds resulting from the foods having a positive electrical charge of from $10^{-9}$ to $10^{-7}$ coulombs.

2. The composition according to claim 1 wherein said composition includes calcium components and wherein said calcium components have a positive residual electrical charge of from $10^{-9}$ to $10^{-7}$ coulombs.

3. A method for increasing growth rate and decreasing feed to gain ratio in animals comprising administering to the animals a feed composition having a proper nutritional balance and a strengthened positive valency of the feed composition resulting from the feed composition having a positive electrical charge of from $10^{-9}$ to $10^{-7}$ coulombs.

4. The method for increasing growth rate and decreasing feed to gain ratio in animals according to claim 3 wherein said feed composition is administered to cattle.

5. The method for increasing growth rate and decreasing feed to gain ratio in animals according to claim 3 wherein said composition of feeds include calcium components and wherein said calcium components have a positive electrical charge of from $10^{-9}$ to $10^{-7}$ coulombs.

6. The method for increasing growth rate and decreasing feed to gain ratio in animals according to claim 5 wherein said feed composition in administered to cattle and results in a weight gain rate of at least about six percent (6%) greater than weight gain rate of cattle administered feed composition without positive electrical charge of from $10^{-9}$ to $10^{-7}$ coulombs.

7. The method for increasing growth rate and decreasing feed to gain ratio in cattle according to claim 5 wherein feed conversion was at least about 5.0% more efficient for cattle administered feed composition without positive charge of from $10^{-9}$ to $10^{-7}$ coulombs.

* * * * *